United States Patent [19]

Varsanyi et al.

[11] 4,064,265
[45] Dec. 20, 1977

[54] DITHIOCARBAMIC ACID ESTERS

[75] Inventors: Denis V. Varsanyi, Rheinfelden; Ernst Aufderhaar, Kaiseraugst; Ernst Schweizer, Arlesheim, all of Switzerland

[73] Assignee: Ciba-Geigy Corporation, Ardsley, N.Y.

[21] Appl. No.: 699,015

[22] Filed: June 23, 1976

[30] Foreign Application Priority Data

July 3, 1975 Switzerland .................... 8673/75

[51] Int. Cl.² .................... A61K 31/27; A61K 31/275; C07C 153/00
[52] U.S. Cl. ................... 424/300; 260/455 A; 424/304
[58] Field of Search ................... 260/455 A; 424/300, 424/286, 304

[56] References Cited
U.S. PATENT DOCUMENTS 3,923,854  12/1975  Duerr .......................... 260/455 A Primary Examiner—Sam Rosen
Attorney, Agent, or Firm—Theodore O. Groeger

[57] ABSTRACT

The present invention relates to new dithiocarbamic acid esters having the formula

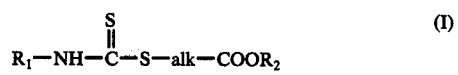

wherein $R_1$ represents a phenyloxyphenyl or phenylaminophenyl radical which is unsubstituted or substituted by lower alkyl, halogen, trifluoromethyl, nitro or cyano, $R_2$ represents hydrogen or lower alkyl, and alk represents lower alkylidene or lower alkylene, and also to salts of compounds of the formula (I), wherein $R_2$ represents hydrogen, with pharmaceutically acceptable bases. These new compounds possess a strong anthelminthic activity and are useful for the treatment of warm-blooded animals infected with parasitic helminths. A specific embodiment is the N-[4-(4-nitroanilino)-phenyl]-dithiocarbamic acid-(2-carboxyethyl)-ester.

22 Claims, No Drawings

DITHIOCARBAMIC ACID ESTERS

DETAILED DESCRIPTION

The present invention provides new dithiocarbamic acid esters, in particular those of the formula

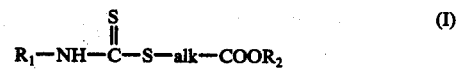

wherein $R_1$ represents a phenyloxyphenyl or phenylaminophenyl radical which is unsubstituted or substituted by lower alkyl, halogen, trifluoromethyl, nitro or cyano, $R_2$ represents hydrogen or lower alkyl, and alk represents lower alkylidene or lower alkylene, and also salts of compounds of the formula (I), wherein $R_2$ represents hydrogen, with pharmaceutically acceptable bases, as well as pharmaceutical preparations which contain these new substances and the administration of these new substances to warm-blooded animals infected with parasitic helminths. A phenyloxyphenyl or phenylaminophenyl radical is primarily a corresponding 4-phenyloxyphenyl or 4-phenylaminophenyl radical the phenyloxy or phenylamino grouping of which is preferably substituted and a substituent is chiefly in 4-position of this grouping.

Lower alkyl contains preferably 1 to 4 carbon atoms and is, for example, methyl, ethyl, n-propyl, isopropyl, n-butyl, isobutyl or tert.butyl.

Halogen preferably represents halogen with an atomic number up to 35, in particular fluorine or bromine and above all chlorine.

Lower alkylidene represented by alk contains in particular up to 4 carbon atoms and is preferably unbranched but can also be branched. Such a radical is in particular methylene, but can also be ethylidene or isobutylidene.

Lower alkylene represented by alk is preferably unbranched lower alkylene, but can also be a branched lower alkylene radical and is, for example, ethylene, 1- or 2-methyl-ethylene, 1,3-propylene, 1-, 2- or 3-methyl-1,3-propylene or 1,4-butylene.

Salts of compounds of the formula I, wherein $R_2$ represents hydrogen, are primarily pharmaceutically useful salts with bases, such as metal or ammonium salts, such as alkali metal or alkaline earth metal salts, for example lithium, sodium or potassium salts, or salts with ammonia.

The new compounds exhibit a useful antiparasitic action, in particular against parasitic helminths. By way of illustration, they act with very good tolerance, for example when tested on mice, rats, golden hamsters, Mongolian jirds, dogs, monkeys, or hens, against nematodes, such as ascaridae, for example *Ascaridia galli*, trichostrongylidae, for example *Nippostrongylus brasiliensis* or *Nematospiroides dubius*, ancylostomatidae, for example *Necator americanus* and *Ancylostoma ceylanicum*, and stongylidae; against cestoda, such as *Hymenolepsis nana*, anoplocephalidae and taenidae; and especially against trematoda, such as fasciolidae, for example *Fasciola hepatica*, and above all, schistosoma, for example *Schistosoma mansoni*, *Schistosoma japonicum* and *Schistosoma hematobium*; and also against the pathogens of filariasis, for example *Dipetalonema witei* and *Litomosoides carinii*, and of malaria, for example *Plasmodium berghei*. In the treatment for example of mice with a 6 to 8 weeks old infection of *Schistosoma mansoni*, *Schistosoma japonicum* or *Schistosoma hematobium*, the compounds of the present invention have an $ED_{50}$ when administered once p.o. (for example with a stomach prove) from app. 10 mg/kg and a curative dose from app. 25 mg/kg. In the treatment of filariasis in Mongolian jirds, the compounds of the present invention prove to be both macro- and microfilaricides when administered once p.o. in a curative dose from app. 200 mg/kg in infections with *Dipetalonema witei* and from app. 50 mg/kg in infections with *Litomosoides carinii*. The compounds of this invention can therefore be used for the treatment of warm-blooded animals in infections with parasitic helminths, such as those referred to hereinabove, especially in the treatment of bilharziasis and filariasis.

The invention provides in the first instance compounds of the formula I, wherein $R_1$ represents 4-phenyloxyphenyl or 4-phenylaminophenyl which is unsubstituted or substituted by methyl, chlorine, trifluoromethyl, cyano and/or especially nitro, a substituent being primarily in the phenyloxy or phenylamino radical and preferably in 4-position of this radical, $R_2$ represents hydrogen, and alk represents the radical of the formula $-(CH_2)_n-$, wherein $n$ is 1, 2 or 3, and salts, chiefly pharmaceutically acceptable salts, such as alkali metal, alkaline earth metal or ammonium salts thereof.

The invention provides in particular compounds of the formula I, wherein $R_1$ represents 4-(4-nitrophenyloxy)-phenyl or 4-(4-nitro-phenylamino)-phenyl, $R_2$ represents hydrogen, and alk represents the radical of the formula $-(CH_2)_n-$, wherein $n$ is as defined hereinabove and is especially 2, and salts, in particular pharmaceutically acceptable salts, such as alkali metal, alkaline earth metal or ammonium salts thereof.

The compounds of the present invention are obtained in known manner. For example, they are obtained by reacting an isothiocyanate compound of the formula $R_1-N=C=S$ (II) with a mercaptoalkanecarboxylic acid compound of the formula $HS-alk-COOR_2$ (III), and, if desired, converting a resultant salt into the free compound and/or a resultant compound of the formula I, wherein $R_2$ represents hydrogen, into a salt.

The above reaction is carried out in the absence, or preferably in the presence, of a suitable inert, in particular polar, solvent or diluent, such as dimethyl formamide or dimethyl sulphoxide, if desired or necessary with cooling or warming (normally in a temperature range of app. 0° C to app. 50° C, preferably of app. 10° C to app. 30° C), and/or in an inert gas atmosphere, such as a nitrogen atmosphere.

The starting materials of the formulae II and III are known or they can be obtained in known manner.

The compounds of the present invention of the formula I can also be obtained by reacting a salt of a dithiocarbamic acid of the formula

with a compound of the formula $X-alk-COOR_2$ (V), wherein X represents a reactive esterified hydroxyl group, or with propiolactone, with acrylic acid or a salt thereof, or with a lower alkyl ester of acrylic acid, and, if desired, carrying out the additional process steps.

The salt of a compound of the formula IV is primarily a metal salt, in particular an alkaline earth metal salt and above all an alkali metal salt, such as a sodium or potassium salt, and also an ammonium salt. A reactive esterified hydroxyl group X is in particular halogen, preferably with an atomic number greater than 9, chiefly chlorine or bromine, and also iodine, and is in addition an organic sulphonyloxy group, such as lower alkylsulphonyloxy, for example methylsulphonyloxy, or arylsulphonyloxy, for example 4-methylphenylsulphonyloxy, 4-bromophenylsulphonyloxy or 3-nitrophenylsulphonyloxy.

The reaction is carried out in known manner, for example in the absence or presence of solvents or diluents, such as dimethyl formamide or dimethyl sulphoxide, if necessary with cooling or warming in a closed vessel and/or in an inert gas atmosphere, for example in a nitrogen atmosphere.

The starting materials of the formula IV can be obtained in known manner, for example by treating an aniline compound of the formula $R_1—NH_2$ (VI) with carbon disulphide in the presence of aqueous ammonia, or with an alkali metal xanthogenate, such as potassium ethyl xanthogenate. The most important compounds of the formula V are — like the specifically mentioned starting materials — known and they can be obtained in similar manner to the known ones.

The compounds of the present invention of the formula I, in which $R_2$ represents hydrogen, i.e. the free carboxylic acids encompassed by this formula, also can be obtained by solvolysis of one of their functional derivatives. The solvolysis is in particular a hydrolysis, which is preferably carried out in an acid medium, for example in hydrochloric acid or dilute sulphuric acid, to which a water-miscible organic solvent, for example a lower alkanol, such as methanol or ethanol, or dioxan, can be added, if necessary with warming. Functional derivatives of carboxylic acids falling under the formula I which are suitable for the solvolysis are, for example, the lower alkyl esters which are also encompassed by this formula and which can be obtained by one of the two processes mentioned hereinbefore, and also the nitriles which can be obtained in a manner analogous to the second process, for example by addition of salts of dithiocarbamic acids of the formula IV to acrylonitrile or reaction of the cited salts with halogeno-lower alkanoic acid nitriles in known manner, as well as the amides which can also be obtained in known manner from the nitriles by addition of water or partial hydrolysis or by reacting salts of dithiocarbamic acids of the formula IV with halogeno-lower alkyl alkanoic acid amides or with acrylic amide.

Resultant salts of compounds of the formula I, wherein $R_2$ represents hydrogen, can be converted into the free compounds by treatment with an acid, such as a mineral acid, for example hydrochloric acid or sulphuric acid.

Compounds of the formula I, wherein $R_2$ represents hydrogen, can be converted in known manner into salts, for example by treating the free acid with the equivalent amount of a base, such as an alkali metal hydroxide or alkaline earth metal hydroxide or ammonia, in a suitable solvent or diluent, such as dimethyl formamide or dimethyl sulphoxide, and concentrating the reaction mixture.

The invention also comprises those embodiments of the processes in which compounds occurring as intermediates are used as starting materials and the missing process steps are carried out with these, or in which the process is discontinued at any stage, or in which starting materials are used in the form of derivatives or are formed during the reaction.

Preferably those starting materials are used and the reaction conditions so chosen that the compounds which have been cited at the outset as being particularly preferred are obtained.

The compounds of the present invention are preferably used in the form of pharmaceutical preparations which are suitable primarily for oral administration.

The pharmaceutical preparations, which also form an object of the present invention, contain from app. 10% to app. 95% of the pharmacological active substance. Preparations for oral administration are preferred, for example dragees, tablets or capsules, and also suspensions. The solid preparations contain per dosage unit form from app. 0.1 g to app. 1.5 g, preferably from app. 0.25 to app. 1 g, of active substance, whereas preparations in liquid form contain from app. 0.5% to app. 15% of active substance.

The pharamaceutical preparations are obtained in known manner, for example by means of conventional mixing, granulating and tabletting methods. For example, pharmaceutical preparations which are suitable for oral administration are obtained by combining the active substance, which, if desired, can be in micronised form, with solid carriers, if appropriate granulating a mixture obtained, and processing the mixture or granulate, if desired and/or if appropriate after adding suitable adjuvants, to tablets or dragee cores.

Suitable carriers are in particular fillers, such as sugar, for example lactose, saccharose, mannitol, or sorbitol, cellulose preparations and/or calcium phosphates, for example tricalcium phosphate or calcium hydrogen phosphate, and binders, such as starch pastes using, for example, maize, wheat, rice or potato starch, gelatin, tragacanth, methyl cellulose, hyroxypropyl methyl cellulose, sodium carboxymethyl cellulose and/or polyvinyl pyrrolidone, and/or, if desired, adjuncts for controlling disintegration, such as the starches mentioned hereinabove, crosslinked polyvinyl pyrrolidone, agar, alginic acid or a salt thereof, such as sodium alginate. Adjuvants are primarily glidants and lubricants, for example silica, talc, stearic acid or salts thereof, such as magnesium or calcium stearate, and/or polyethylene glycol. Dragee cores are provided with suitable, if appropriate stomach-resistant, coatings, using, inter alia, concentrated sugar solutions which can contain gum arabic, talc, polyvinyl pyrrolidone, polyethylene glycol and/or titanium dioxide, lacquer solutions in suitable organic solvents or solvent mixtures, or, for preparing stomach-resistant coatings, using solutions of suitable cellulose preparations, such as acetyl cellulose phthalate or hydroxypropylmethyl cellulose phthalate. Dyes or pigments can be added to the tablets or dragee coatings, for example in order to identify or indicate different dosages of active substance.

Further pharmaceutical preparations for oral administration are push-fit capsules of gelatin, and soft sealed capsules of gelatin and a plasticiser, such as glycerol or sorbitol. The push-fit capsules can contain the active substance in the form of a granulate, for example in admixture with fillers such as maize starch, binders and/or glidants, such as talc or magnesium stearate, and, if appropriate, stabilisers. In soft capsules, the active substance is preferably dissolved or suspended in suitable liquids, such as fat oils, paraffin oil or liquid polyethylene glycols, and stabilisers can also be added.

Suspensions for oral administration are primarily aqueous suspensions, which contain, for example, stabilisers for raising the viscosity and delaying sedimentation, such as water-soluble cellulose ethers, for example carboxymethyl cellulose and salts thereof, such as the sodium salt, or methyl cellulose, and wetting agents, such as sodium lauryl sulphate or dioctyl sodium sulphosuccinate, or non-ionogenic wetting agents, such as polyoxyethylene sorbitan fatty acid esters or polyethylene glycolpolypropylene glycol-copolymers, and to which can be added, if desired or necessary, preservatives, such as 4-hydroxybenzoic acid lower alkyl esters, such as the corresponding methyl, ethyl or n-propyl esters, and/or aromatic substances and/or sweeteners.

It is a further object of the invention to provide a method of treating infections caused by parasitic helminths in warm-blooded animals, said method comprising the administration of the compounds of the formula I or salts thereof, and wherein the above pharmaceutical preparations are used primarily for oral administration, a single dose of app. 0.25 g to app. 1.5 g, preferably of app. 0.5 g to app. 1 g, of active substance being administered to a warm-blooded animal of approximately 70 kg body weight.

EXAMPLE 1

A solution of 27.2 g of 4-(4-nitrophenyloxy)-phenylisothiocyanate (m.p. 124°–125° C) and 10 ml of 3-mercaptopropionic acid in 250 ml of anhydrous dimethyl formamide is stirred at room temperature. When the reaction is complete, the solution is poured, with stirring, into 250 ml of water. The resultant fine precipitate is collected by filtration, washed with water and dried under reduced pressure to yield the N-[4-(4-nitrophenyloxy)-phenyl]-dithiocarbamic acid-(2-carboxyethyl)-ester with a melting point of 146° C.

EXAMPLE 2

To a solution of 8.13 g of 4-(4-nitroanilino)-phenylisothiocyanate (m.p. 204°–206° C) in 75 ml of anhydrous dimethyl formamide are added dropwise 3.66 g of 3-mercaptopropionic acid. The mixture is stirred for 48 hours at room temperature, poured with good stirring into 1000 ml of water and stirring is continued for a further hour at 0°–5° C. The crystalline precipitate is collected by filtration and suspended 3 times in 150 ml of cold water on each occasion and filtered each time. The resultant N-[4-(4-nitroanilino)-phenyl]-dithiocarbamic acid-(2-carboxyethyl)-ester melts at 163°–165° C.

The following compounds can be obtained in analogous manner using the appropriate starting materials:

N-[4-(4-nitroanilino)-phenyl]-dithiocarbamic acid-(carboxymethyl)-ester, for example by treating 4-isothiocyanato-4'-nitro-diphenylamine with 2-mercaptoacetic acid;

N-[4-(4-nitroanilino)-phenyl]-dithiocarbamic acid-(1-carboxyethyl)-ester, for example by treating 4-isothiocyanato-4'-nitrodiphenylamine with 2-mercaptopropionic acid;

N-[4-(4-nitroanilino)-phenyl]-dithiocarbamic acid-(3-carboxypropyl)-ester, for example by treating 4-isothiocyanato-4'-nitrodiphenylamine with 4-mercaptobutyric acid;

N-[4-(4-nitroanilino)-phenyl]-dithiocarbamic acid-(2-ethoxycarbonylethyl)-ester, for example by treating 4-isothiocyanato-4'-nitro-diphenylamine with 3-mercapto-propionic acid ethyl ester;

N-[4-(2-nitroanilino)-phenyl]-dithiocarbamic acid-(2-carboxyethyl)-ester, for example by treating 4-isothiocyanato-2'-nitro-diphenylamine (m.p. 158°–159° C) with 3-mercapto-propionic acid;

N-[4-(3-nitroanilino)-phenyl]-dithiocarbamic acid-(2-carboxyethyl)-ester, for example by treating 4-isothiocyanato-3'-nitro-diphenylamine (m.p. 117° C) with 3-mercapto-propionic acid;

N-[4-(2,4-dinitroanilino)-phenyl]-dithiocarbamic acid-(2-carboxyethyl)-ester, for example by treating 4-isothiocyanato-2',4'-dinitro-diphenylamine (m.p. 134°–136° C) with 3-mercapto-propionic acid;

N-[4-(4-chloroanilino)-phenyl]-dithiocarbamic acid-(2-carboxyethyl)-ester, for example by treating 4-chloro-4'-isothiocyanato-diphenylamine (m.p. 110°–112° C) with 3-mercapto-propionic acid;

N-[4-(4-methylanilino)-phenyl]-dithiocarbamic acid-(2-carboxyethyl)-ester, for example by treating 4-isothiocyanato-4'-methyl-diphenylamine m.p. 64°–66° C) with 3-mercapto-propionic acid;

N-[4-(4-cyanoanilino)-phenyl]-dithiocarbamic acid-(2-carboxyethyl)-ester, for example by treating 4-cyano-4'-isothiocyanato-diphenylamine (m.p. 185°–186° C) with 3-mercapto-propionic acid; and N-[4-(3-trifluoromethylanilino)-phenyl]-dithiocarbamic acid-(2-carboxyethyl)-ester, for example by treating 4-isothiocyanato-diphenylamine (m.p. 77°–79° C) with 3-mercapto-propionic acid.

EXAMPLE 3

To a solution of 9.5 g of 4-(4-nitroanilino)-phenylisothiocyanate in 80 ml of dimethyl formamide are added dropwise 9.6 g of mercapto-acetic acid ethyl ester in the course of 10 minutes and the mixture is stirred for 40 hours. The solution is then stirred into 2 liters of water. The precipitate of N-[4-(4-nitroanilino)-phenyl]-(ethoxycarbonylmethyl)-ester which has formed is collected by suction filtration, thoroughly washed with water and dried under reduced pressure. Melting point: 130°–131° C.

EXAMPLE 4

Tablets containing 0.5 g of N-[4-(4-nitroanilino)-phenyl]-dithiocarbamic acid-(2-carboxyethyl)-ester can be obtained as follows:

| Composition (for 10,000 tablets): | |
|---|---|
| N-[4-(4-nitroanilino)-phenyl]-dithiocarbamic acid (2-carboxyethyl)-ester | 5000 g |
| wheat starch | 790 g |
| stearic acid | 30 g |
| magnesium stearate | 30 g |
| talc | 400 g |
| water | as required |

A mixture of the N-[4-(4-nitroanilino)-phenyl]-dithiocarbamic acid-(2-carboxyethyl)-ester and 500 g of wheat starch is made into a paste with app. 1300 g of demineralised water and the paste is uniformly moistened with a further 600 g of demineralised water. The mixture is kneaded to a slightly plastic mass and forced through a sieve with a mesh size of app. 3 mm. The granulate is thereafter dried and again forced through a sieve. The magnesium stearate, stearic acid, talc and 290 g of wheat starch are mixed with the granulate which has been brought to a uniform granular size, and the mixture is pressed to tablets of 0.625 g.

What we claim is:

1. A dithiocarbamic acid ester of the formula

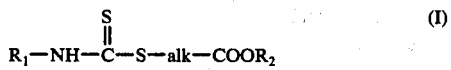

wherein $R_1$ represents a phenyloxyphenyl or phenylaminophenyl radical which is unsubstituted or substituted by lower alkyl, halogen, trifluoromethyl, nitro or cyano, $R_2$ represents hydrogen or lower alkyl, and alk represents lower alkylidene or lower alkylene, and the salts of a compound of the formula I, wherein $R_2$ represents hydrogen, with pharmaceutically acceptable bases.

2. A compound according to claim 1 having the formula I, wherein $R_1$ and alk have the meanings given in claim 1 and $R_2$ represents hydrogen, and its salts with pharmaceutically acceptable bases.

3. A compound according to claim 1 having the formula I, wherein $R_1$ and alk have the meanings given in claim 1 and $R_1$ represents lower alkyl.

4. A compound according to claim 1 having the formula I, wherein $R_1$ represents 4-phenyloxyphenyl or 4-phenylaminophenyl which is unsubstituted or substituted by methyl, chlorine, trifluoromethyl, nitro or cyano, $R_2$ represents hydrogen or lower alkyl, and alk represents the radical of the formula $-(CH_2)_n-$, wherein $n$ is 1, 2 or 3, and the salts of a compound of the formula I, wherein $R_2$ represents hydrogen, with pharmaceutically acceptable bases.

5. A compound according to claim 1 having the formula I, wherein $R_1$ represents 4-phenyloxyphenyl or 4phenylaminophenyl which is unsubstituted or substituted by methyl, chlorine, trifluoromethyl, nitro or cyano, $R_1$ represents hydrogen and alk represents the radical of the formula $-(CH_2)_n-$, wherein $n$ is 1, 2 or 3, and its salts with pharmaceutically acceptable bases.

6. A compound according to claim 1 having the formula I, wherein $R_1$ represents 4-phenyloxyphenyl or 4-phenylaminophenyl which is unsubstituted or substituted by methyl, chlorine, trifluoromethyl, nitro or cyano, $R_1$ represents lower alkyl, and alk represents the radical of the formula $-(CH_2)_n-$, wherein $n$ is 1, 2 or 3.

7. A compound according to claim 1, wherein $R_1$ represents 4-(4-nitrophenyloxy)-phenyl or 4-(4-nitrophenylamino)-phenyl, $R_2$ represents hydrogen or lower alkyl, and alk represents the radical of the formula $-(CH_2)_n-$, wherein $n$ is 1, 2 or 3, and the salts of a compound of the formula I, wherein $R_2$ represents hydrogen, with pharmaceutically acceptable bases.

8. A compound according to claim 1 having the formula I, wherein $R_1$ represents 4-(4-nitrophenyloxy)-phenyl or 4-(4-nitrophenylamino)-phenyl, $R_1$ represents hydrogen and alk represents the radical of the formula $-(CH_2)_n-$, wherein $n$ is 1, 2 or 3, and its salts with pharmaceutically acceptable bases.

9. A compound according to claim 1 having the formula I wherein $R_1$ represents 4-(4-nitrophenyloxy)-phenyl or 4-(4-nitrophenylamino)-phenyl, $R_1$ represents lower alkyl and alk represents the radical of the formula $-(CH_2)_n-$, wherein $n$ is 1, 2 or 3.

10. A compound according to claim 1 which is N-[4-(4-nitrophenyloxy)-phenyl]-dithiocarbamic acid-(2-carboxyethyl)-ester.

11. A compound according to claim 1 which is a salt of the N-[-4-(4-nitrophenyloxy)-phenyl]-dithiocarbamic acid-(2-carboxyethyl)-ester with a pharmaceutically acceptable base.

12. A compound according to claim 1 which is N-[4-(4-nitroanilino)-phenyl]-dithiocarbamic acid-(2-carboxyethyl)-ester.

13. A compound according to claim 1 which is a salt of the N-[4-(4-nitroanilino)-phenyl]-dithiocarbamic acid-(2-carboxyethyl)-ester with a pharmaceutically acceptable base.

14. A compound according to claim 1 which is N-[4-(4-nitroanilino)-phenyl]-dithiocarbamic acid-[(ethoxycarbonyl)-methyl]-ester.

15. A method for the treatment of infections with parasitic helminths in a warm-blooded animal comprising administration to said animal of an antihelminthically effective amount of a compound according to claim 1 having the formula

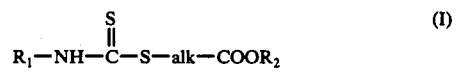

wherein $R_1$ represents a phenyloxyphenyl or phenylaminophenyl radical which is unsubstituted or substituted by lower alkyl, halogen, trifluoromethyl, nitro or cyano, $R_2$ represents hydrogen or lower alkyl, and alk represents lower alkylidene or lower alkylene, or of a salt of a compound of the formula I, wherein $R_2$ represents hydrogen, with a pharmaceutically acceptable base.

16. A method according to claim 15 wherein an anthelminthically effective amount of N-[4-(4-nitroanilino)-phenyl]-dithiocarbamic acid-(2-carboxyethyl)-ester is administered.

17. A method according to claim 15 wherein an anthelminthically effective amount of a salt of the N-[4-(4-nitroanilino)-phenyl]-dithiocarbamic acid-(2-carboxyethyl)-ester with a pharmaceutically acceptable base is administered.

18. A pharmaceutical preparation for the treatment of warm-blooded animals infected with parasitic helminths comprising an anti-helminthically effective amount of a compound according to claim 1 having the formula

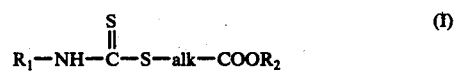

wherein $R_1$ represents a phenyloxyphenyl or phenylaminophenyl radical which is unsubstituted or substituted by lower alkyl, halogen, trifluoromethyl, nitro or cyano, $R_2$ represents hydrogen or lower alkyl, and alk represents lower alkylidene or lower alkylene, or of a salt of a compound of the formula I, wherein $R_2$ represents hydrogen, with a pharmaceutically acceptable base, in aqueous suspension or in admixture with a solid pharmaceutical carrier.

19. A pharmaceutical preparation according to claim 18, wherein the anthelminthically effective compound is such of formula I, wherein $R_1$ represents 4-phenyloxyphenyl or 4-phenylaminophenyl which is unsubstituted or substituted by methyl, chlorine, trifluoromethyl, nitro or cyano, $R_2$ represents hydrogen or lower alkyl, and alk represents the radical of the formula $-(CH_2)_n-$, wherein $n$ is 1, 2 or 3, or a salt of said compound of the formula I, wherein $R_2$ represents hydrogen, with a pharmaceutically acceptable base.

20. A pharmaceutical preparation according to claim 18, wherein the anthelminthically effective compound is such of formula I, wherein $R_1$ represents 4-(4-nitrophenyloxy)-phenyl or 4-(4-nitrophenylamino)-phenyl, $R_2$ represents hydrogen or lower alkyl, and alk represents the radical of the formula $-(CH_2)_n-$, wherein $n$ is 1, 2 or 3, or a salt of said compound of the formula I, wherein $R_2$ represents hydrogen, with a pharmaceutically acceptable base.

21. A pharmaceutical preparation according to claim 18, wherein the anthelminthically effective compound is the N-[4-(4-nitroanilino)-phenyl]-dithiocarbamic acid-(2-carboxyethyl)-ester.

22. A pharmaceutical preparation according to claim 18, wherein the anthelminthically effective compound is a salt of the N-[4-(4-nitroanilino)-phenyl]-dithiocarbamic acid-(2-carboxyethyl)-ester with a pharmaceutically acceptable base.